United States Patent [19]

Ishigaki

[11] Patent Number: 4,956,187

[45] Date of Patent: Sep. 11, 1990

[54] PROCESS FOR PREPARING IRON ENRICHED FOOD PRODUCTS

[75] Inventor: Reisaburo Ishigaki, Numazu, Japan

[73] Assignee: Terumo Kabushiki Kaisha, Tokyo, Japan

[21] Appl. No.: 269,179

[22] PCT Filed: Apr. 20, 1987

[86] PCT No.: PCT/JP87/00249

§ 371 Date: Dec. 15, 1988

§ 102(e) Date: Dec. 15, 1988

[87] PCT Pub. No.: WO87/06103

PCT Pub. Date: Oct. 22, 1987

[30] Foreign Application Priority Data

Apr. 19, 1986 [JP] Japan .................................. 61-90899
Jan. 23, 1987 [JP] Japan .................................. 62-13680

[51] Int. Cl.⁵ ........................... A23L 1/20; A23L 1/214
[52] U.S. Cl. .................................. 426/46; 426/52; 426/62; 426/64; 426/74
[58] Field of Search ............. 426/46, 49, 52, 7, 61-62, 426/74

[56] References Cited

FOREIGN PATENT DOCUMENTS

| | | |
|---|---|---|
| 54-157890 | 12/1979 | Japan . |
| 56-50816 | 12/1981 | Japan . |
| 56-158088 | 12/1981 | Japan . |
| 58-101686 | 6/1983 | Japan . |
| 60-104016 | 6/1985 | Japan . |
| 3167757 | 7/1988 | Japan ...................................... 426/52 |
| 1395274 | 5/1988 | U.S.S.R. ................................. 426/52 |

*Primary Examiner*—Marianne Cintins
*Attorney, Agent, or Firm*—Burns, Doane, Swecker & Mathis

[57] ABSTRACT

There is provided a process for preparing iron enriched food products by hydrolyzing pulverized soybean, pulverized carrot or a mixture of the two with saccharide-decomposing enzyme and cultivating yeast in said hydrolyzate in the presence of an iron compound. The food products produced by the process not only contain iron in readily absorbable and adverse reaction-free form but also are rich in nutritive elements derived from soybean and carrot so that they are very useful as meal for patients.

19 Claims, No Drawings

PROCESS FOR PREPARING IRON ENRICHED FOOD PRODUCTS

TECHNICAL FIELD

The present invention relates to a process for preparing iron enriched fermented food products.

BACKGROUND TECHNOLOGY

In olden times a dish of carrots, sea tangle ("Kombu") and soybeans cooked together in an iron pan had widely been eaten as a daily dish. Recently, however, the use of iron pots has become unpopular so that it is no longer a source of iron supply. In the preparation of soybean cake ("Miso") or soybean sauce ("Shoyu"), the starting soybeans are boiled in an iron pot and then combined with rice malt (Koji) to be processed to "Miso" or combined with parched wheat to make "Koji" to be processed to "Shoyu". The iron which is derived from an iron pot used in the course of preparing "Shoyu" or "Miso" reacts with lactic acid producing during the fermentation process and is converted to an organic form or and is introduced into the yeast cells. However, iron that remains in an organic form in fermented products causes deterioration in the color of the products with time. Therefore the fermentation equipment containing iron to produce the fermentation products is no longer used. Consequently, these fermentation products are no longer a source of iron supply. On the other hand, mixtures of ferric citrate or ferrous lactate with a plant extract have heretofore been used for supplying iron but occasionally have caused inflammation on or around the lips or anorexia.

We previously developed a process for preparing fermented food products of soybean by digesting boiled and powdered raw soybeans with a digestive enzyme and then fermenting the digest with yeast, in which a patent application was filed (Japanese Patent Publication No. 50816/81). According to the preparative process fermented food products of soybeans, which do not contain unpleasant color and odor caused by the growth of fungi and bacteria, are produced. Whereas soybeans are a nutritious food rich in protein, lipid and saccharide, its iron content is as low as 10 mg or below per 100 g of edible part. As a result of extensive studies for reinforcing the iron content in the above-mentioned fermented food products of soybeans, we have found that the iron enriched food products having good flavor and high nutritive value are obtained by digesting pulverized soybeans and cultivating yeast in the digest in the presence of an iron compound.

Also provided are iron enriched food products having good flavor and being rich in carotene by digesting pulverized carrots and cultivating yeast in the digest in the presence of an iron compound.

Furthermore, there are provided iron enriched food products having very high nutritive value and being rich in iron in readily absorbable form, by digesting pulverized soybeans and pulverized carrots and cultivating yeast in the digest mixture in the presence of an iron compound.

DISCLOSURE OF THE INVENTION

The present invention has been undertaken on the basis of the above findings and comprises:

1. A process for preparing an iron enriched food product which comprises hydrolyzing pulverized soybeans, pulverized carrots or a mixture of the two with a saccharide-decomposing enzyme and a cultivating yeast in said hydrolyzate in the presence of an iron compound.

2. A process according to item 1, wherein pulverized and boiled soybeans produced by mixing powdered raw soybeans having sizes not larger than 200 mesh, with hot water and boiling the mixture, said powdered raw soybeans being obtained by finely pulverizing skinned raw soybeans, or boiled and pulverized carrots producted by boiling carrots and pulverizing the boiled carrots, or a mixture of the two are hydrolyzed with amylase, and *Saccharomyces cerevisiae* is cultivated in said hydrolyzate in the presence of an iron compound.

3. A process according to item 1 or 2 wherein the iron compound is iron citrate or iron lactate.

In carrying out the process of the present invention, skinned raw soybeans are finely pulverized to obtain fine powders with sizes of not larger than 200 mesh. The above step facilitates dissolution of the water-soluble components of soybeans, which in turn makes the soybeans more sensitive to hydrolase. Preferably, the powdered raw soybeans are mixed with hot water, and the mixture is rapidly boiled to inactivate enzymes present in the powdered raw soybeans. When carrots are employed, water is added to the raw carrots, which are then wet pulverized. Preferably, the carrots is cooked before pulverization. To the pulverized soybeans or carrots, or a mixture of the two is added a saccharide-decomposing enzyme to hydrolyze saccharides in the starting material such as starch and cellulose for saccharification. The starting soybeans or carrots are used in an amount so as to give a saccharide concentration of 1-250 g/l after hydrolysis. Soybeans at a level of 3-700 g/l, preferably 3-350 g/l, on a dry basis or carrots at a level of 1.5-390 g/l, preferably 1.5-200 g/l, on a dry basis are used alone or in an appropriate combination. If soybeans and carrots are employed in combination, the soybeans are present in an amount of 1-90 parts, preferably 1-50 parts per a total of 100 parts by weight (dry basis). As the saccharide-decomposing enzymes are employed amylases, cellulases or the like. As the amylases $\alpha$-amylase, $\beta$-amylase, glucoamylase, isoamylase and the like may be used. The saccharization is conducted under conditions to allow the addition of an enzyme at a ratio of 1/1000–3/1000 (by weight) to the substrate, at a temperature of 10°–50° C. or 10°–90° C. for a heat-resistant enzyme for a period of 10 min.–5 hours, these being variable depending upon the activity of the enzyme. The saccharide concentration of the hydrolyzate is desirably in the range of about 1–250 g/l. After completion of the hydrolysis, an iron compound is added to the resulting hydrolyzate, and the mixture is innoculated with yeast followed by cultivation. The iron compound may be added before the hydrolysis step, and the amount to be added (concentration in the culture) is desirably in the range of about 250–15000 m/l. There is no particular limitation to the nature of the iron compound, which may be an organic or inorganic ferrous or ferric compound. For example, ferric chloride, ferrous or ferric sulfate, iron citrate, iron tartrate, ferrous lactate, ferrous gluconate, ferrous or ferric pyrophosphate, ferric cholineisocitrate and the like are used. It is preferable to employ *Saccharomyces cerevisiae* as the yeast. The amount of yeast used (concentration in the culture) is in the range of 5–300 g/l for raw yeast or 2–150 g/l for dry yeast. Cultivation is carried out usually at 5°-50° C. and preferably at 10°-30° C. for a period of 30 min. to 4 days.

It is preferred to neutralize the organic acids which have been formed in the culture during the above-mentioned cultivation of yeast with calcium carbonate to a pH of approximately 5. The neutralization improves strong acid taste and also achieves enrichment of calcium. The culture thus obtained is used as is or dried by a conventional method to yield an iron enriched food product. Freeze drying, spray drying, hot air drying, vacuum drying and the like may be adopted, and freeze drying is most preferable.

In the above-described process of the invention, the starting material is a digestion product of pulverized soybeans, pulverized carrots or a mixture of the two so that the introduction of iron into the yeast and the formation of a complex are attained most effectively resulting in excellent absorption of the iron throughout the digestive tract.

The absorption ratio of iron throughout the digestive tract varies depending upon the type of iron used. It greatly differs between an inorganic iron and organic iron, and also between the organic iron existing in plants and the iron in animals widely existing as heme iron. Iorn is absorbed as a divalent iron mainly through the region from the duodenum to the ileum. It is absorbed in the form of reduced iron through cells of the intestinal wall. The absorption ratio of iron alos varies depending upon the moving rate of the iron in the intestinal tract.

Heretofore, ferric citrate or ferrous lactate has been used for iron enrichment in the form of a simple mixture with a plant extract. Although the iron is possibly absorbed in such a form, inflammation on the lips and skin around the lips and adverse reactions such as anorexia are associated with continuous ingestion. The food products of the invention enables ingestion of iron without such adverse side effects.

Moreover, the use of a digestion product containing a mixture of pulverized soybeans and pulverized carrots described in the process of the present invention would provide food products with nutritive elements such as protein, lipid, saccharide and carotene which are abundantly contained in soybeans and carrots, in readily absorbable form and without loss.

In addition, the food products produced from pulverized carrots according to the process of the present invention are thoroughly miscible with oil and exhibit high emulsifying activity, and thus they are also useful as an edible emulsifier.

The invention will be described below in more details with reference to the examples.

EXAMPLE 1

A mixture containing 120 g of powdered and skinned raw soybeans and 240 g of hot water was boiled. 1.0 kg of raw carrots are cooked for 45 min. and then wet pulverized. To the pulverized carrots was added 1.0 kg of warm water so as to maintain the temperature at 40°-45° C. The soybean mixture was blended with the carrot mixture to give a jelly mass to which a digestive enzyme was added at a ratio of 1/1000 based on the substrate. The mixture was subjected to digestion for one hour, and 12 g of ferric citrate was dissolved in the digestion mixture. The resulting mass was inoculated with 300 g of *Saccharomyces cerevisiae* followed by growth and fermentation at 20°-25° C. for two hours. Before completion of the fermentation, organic acids thereby formed, were neutralized with calcium carbonate to adjust the reduced pH to 5.0. A brownish black color, characteristic of ferric citrate, disappeared as the fermentation progressed. The culture was dried to give the desired product.

EXAMPLE 2

A mixture containing 60 g of powdered and skinned raw soybean and 120 g of hot water was boiled. Raw carrots weighing 1.0 kg were boiled for 30 min. and then wet pulverized. To the pulverized carrots was added 1.0 kg of warm water to maintain the temperature at 40°-45° C. The soybean mixture was blended with the carrot mixture to give a liquid mass to which is then added a digestive enzyme at a ratio of 1/1000 based on substrate. The mixture was subjected to digestion for one hour, and 12 g of ferrous lactate was dissolved in the digestion mixture. The resulting mass was inoculated with 300 g of *Saccharomyces cerevisiae* followed by growth and fermentation at 20°-25° C. for two hours. Before completion of the fermentation, organic acids thereby formed are neutralized with calcium carbonate to a pH of 5.0. The culture was dried to give the desired product.

EXAMPLE 3

Powdered and skinned raw soybeans weighing 120 g were mixed with 360 g of hot water, and the mixture was boiled. After cooling to a temperature of 50° C., a digestive enzyme was added to the resulting mixture at a ratio of 1/50 based on the substrate followed by digestion. Centrifugal separation and addition of water were repeated to produce 1000 g of the hydrolyzate. Separately, 1.0 kg of raw carrots were boiled for 30 min. and then wet pulverized. The pulverized carrots were combined with the above hydrolyzate, and further digestion was undertaken at 45° C. for one hour. In the digestion mixture was dissolved 12 g of ferrous lactate, and the resulting mixture was inoculated with 300 g of *Saccharomyces cerevisiae*. Growth and fermentation were carried out at 20°-25° C. for two hours. Before completion of the fermentation organic acids thereby formed, were neutralized with calcium carbonate to adjust the reduced pH to 5. The culture was dried to give the desired product.

EXAMPLE 4

1.0 kg of raw carrots were boiled for 30 min. and then wet pulverized to give a liquid mass. To the mass was added 1.0 kg of warm water to maintain the temperature at 40°-45° C. To the resulting mixture was added amylase at a ratio of 1/1000 to the substrate. Saccharification was carried out for one hour. After inoculation with 300 g of *Saccharomyces cerevisiae*, 12 g of ferrous lactate was disolved therein followed by growth and fermentation at 20°-25° C. for two hours. Before completion of the fermentation organic acids thereby formed, were neutralized with calcium carbonate to adjust the reduced pH. The greenish white color of the ferrous lactate was masked by the color of carotene, but the acids formed were characteristically rich in lactic acid. The culture was used either as is or dried.

EXAMPLE 5

Powdered and skinned raw soybeans weighing 300 g were mixed with 800 g of hot water, and the mixture was boiled for 30 min. Subsequently, while maintaining the temperature at 40°-45° C., 12 g of ferric citrate were dissolved therein, and a commercially available saccharifying enzyme was added at a ratio of 1/1000 to the substrate. The resulting mixture was subjected to saccharification treatment for one hour.

The treated solution was inoculated with 300 g of *Saccharomyces cerevisiae* while maintaining the temperature at 20°–25° C. followed by fermentation, for two hours. Before completion of the fermentation, the pH reduced during the fermentation, was neutralized with calcium carbonate, and the culture was dried to give the desired product.

Test Example 20 female volunteers were given the iron enriched food products obtained in Examples 1 and 2 and a control food product respectively at a daily dose of 1 g (containing 5 mg or more of iron) within 30 min. after every evening meal. The number of persons with occurrence of inflammation on the lips and skin around the lips was counted by age range. Results are shown in Table 1. The control food product is a simple mixture consisting of pulverized and boiled soybeans, boiled and pulverized carrots and ferrous lactate.

TABLE 1

| Tested person | Food product of Example 1 | | | Food product of Example 2 | | | Control food product | | |
|---|---|---|---|---|---|---|---|---|---|
| | Day 2 | Day 4 | Day 6 | Day 2 | Day 4 | Day 6 | Day 2 | Day 4 | Day 6 |
| 15–18 year-old (female) | 0 | 0 | 0 | 0 | 0 | 0 | 0 | 1 | 2 |
| 25–30 year-old (female) | 0 | 0 | 0 | 0 | 0 | 0 | 0 | 2 | 4 |

As evidently demonstrated by the above results, the intake of the food product of the present invention is associated with no adverse reaction at all, while intake of a simple mixture of the components of the invention without yeast fermentation occasionally, caused inflammation on the lips and skin around the lips.

INDUSTRIAL APPLICABILITY

The iron enriched food products according to the present invention not only contain iron in readily absorbable and adverse reaction-free form, but also are rich in nutritive elements such as protein, lipid, saccharide, carotene and calcium so that they are useful as food for patients, especially for iron-deficient patients.

What is claimed is:

1. A process for the preparation of an iron enriched food product comprising the steps of:
   (a) hydrolyzing a substrate comprising pulverized soybeans, pulverized carrots or a mixture thereof with an effective hydrolyzing amount of a saccharide decomposing enzyme at a temperature between 10° C. to 90° C. for a period between 10 minutes to 5 hours to form a hydrolyzate and
   (b) inoculating said hydrolyzate with an effective amount of yeast for cultivation in the presence of an effective amount of an iron compound to enrich said food product at a temperature between 5° C. to 50° C. for a period between 30 minutes to 4 days to form a culture to prepare the desired food product.

2. The process according to claim 1, wherein said saccharide-decomposing enzymes are added to said substrate at a ratio between 1/1000 to 20/1000 by weight.

3. The process according to claim 2, wherein said saccharide-decomposing enzyme is added to said substrate at a ratio between 1/1000 to 3/1000 by weight.

4. The process according to claim 1, wherein said hydrolyzation is carried out at a temperature between 10° C. to 50° C. using non-resistant saccharide-decomposing enzymes.

5. The process according to claim 1, wherein said hydrolyzation is carried out at a temperature between 10° C. to 90° C. using heat-resistant saccharide-decomposing enzymes.

6. The process according to claim 1, wherein said yeast is present in an amount between 5 to 300 g/l is said culture.

7. The process according to claim 6, wherein said yeast is raw yeast or dry yeast.

8. The process according to claim 7, wherein said raw yeast is present in an amount between 5 to 300 g/l in said culture.

9. The process according to claim 7, wherein said dry yeast is present in an amount between 2 to 150 g/l in said culture.

10. The process according to claim 1, wherein said iron compound is added in a concentration between 250 mg/l to 15000 mg/l to said culture.

11. The process according to claim 10, wherein said iron compound is iron citrate or iron lactate.

12. The process according to claim 11, wherein said pulverized soybeans are produced by finely pulverizing skinned raw soybeans to a size less than 200 mesh, mixing said pulverized raw skinned soybeans in hot water and boiling said mixture.

13. The process according to claim 1, wherein said pulverized carrots are produced by boiling carrots and wet pulverizing said carrots.

14. The process according to claim 1, wherein said saccharide-decomposing enzyme is amylase.

15. A process for preparing an iron enriched food product which comprises hydrolyzing pulverized soybeans, pulverized carrots or a mixture thereof with a saccharide-decomposing enzyme at a ratio of 1/1000 to 20/1000 by weight of the substrate, at a temperature of 10° C. to 50° C. using non-heat resistant enzymes and 10° C. to 90° C. using heat-resistant enzymes for a period between 10 minutes to 5 hours to form a hydrolysate; inoculating said hydrolysate with yeast in an amount of 5 to 300 g/l for raw yeast or 2 to 150 g/l for dry yeast and cultivating said inoculated yeast at 5° C. to 50° C. for a period between 30 minutes to 4 days to form a culture, in the presence of between 250 to 15000 mg/l of an iron compound based on the concentration of said culture, to prepare the desired food product.

16. The process according to claim 15, wherein pulverized and boiled soybeans are produced by mixing powdered raw soybeans having a size not larger than 200 mesh with hot water and boiling the mixture, said powdered raw soybeans being obtained by finely pulverizing skinned raw soybeans, or boiled and pulverized carrots, produced by boiling and pulverizing the boiled carrots, or a mixture thereof, is hydrolyzed with amylase, and *Saccharomyces cerevisiae* is cultivated in said resulting hydrolyzate in the presence of an iron compound.

17. The process according to claim 15, wherein the saccharide-decomposing enzyme is added at a ratio between 1/1000 to 3/1000 by weight to the substrate.

18. The process according to claim 15, wherein said iron compound is iron citrate or iron lactate.

19. The process according to claim 15, wherein the cultivation is conducted between 30 minutes to 4 days.

* * * * *